United States Patent [19]

Brackenridge

[11] 3,959,387

[45] *May 25, 1976

[54] RECOVERY OF BROMINATED BIPHENYL OXIDE

[75] Inventor: David R. Brackenridge, Royal Oak, Mich.

[73] Assignee: Ethyl Corporation, Richmond, Va.

[ * ] Notice: The portion of the term of this patent subsequent to Sept. 3, 1974, has been disclaimed.

[22] Filed: Aug. 30, 1974

[21] Appl. No.: 501,983

Related U.S. Application Data

[63] Continuation-in-part of Ser. No. 283,324, Aug. 24, 1972, Pat. No. 3,833,674.

[52] U.S. Cl. ............................................. 260/612 R
[51] Int. Cl.$^2$ ......................................... C07C 41/00
[58] Field of Search .................... 260/612 R, 649 DP

[56] References Cited
UNITED STATES PATENTS

| | | | |
|---|---|---|---|
| 3,763,248 | 10/1973 | Mitchell | 260/649 DP |
| 3,833,674 | 9/1974 | Brackenridge | 260/612 R X |
| 3,845,146 | 10/1974 | Moore et al. | 260/649 DP |

*Primary Examiner*—Bernard Helfin
*Attorney, Agent, or Firm*—Donald L. Johnson; John F. Sieberth; Robert A. Linn

[57] ABSTRACT

A process for preparing polybrominated aromatic compounds which comprises (a) reacting an aromatic compound with bromine in the presence of a metal halide halogenation catalyst and solvent quantities of methylene bromide, and (b) adding a lower alkanol to the thereby produced reaction mixture to precipitate polybrominated aromatic product.

4 Claims, No Drawings

RECOVERY OF BROMINATED BIPHENYL OXIDE

CROSS-REFERENCE TO RELATED APPLICATION

This application is a continuation-in-part of application Ser. No. 283,324, filed Aug. 24, 1972, now U.S. Pat. No. 3,833,674.

BACKGROUND OF THE INVENTION

The halogenation of aromatic compounds is generally known in the art. Halogenated aromatic compounds have found use as flame retardants in various polymer substrates, and processes for their production have become relatively more important.

The difficulty in halogenating aromatics is that the addition of each successive halogen atom deactivates the aromatic nucleus and makes subsequent halogen addition more difficult; for example, the addition of the second chlorine atom to chlorobenzene is more difficult by factor of 8.5:1 when compared with the energy requirement for addition of the first chlorine atom.

In the production of many polybrominated aromatic compounds in which the aromatic nucleus is highly brominated, the reaction is difficult because the product is a solid and tends to agglomerate during the reaction, thus increasing the difficulty of further halogenation that much more.

For example, in a process for producing polybrominated aromatic compounds, several recent patents have suggested the use of fuming sulfuric acid (oleum) as a suitable reaction medium (see U.S. Pat. Nos. 3,232,959 and 3,285,995). The sulfuric acid acts as a solvent; and sulfur trioxide oxidizes the hydrogen bromide back to bromine, thus permitting complete utilization of bromine. However, this process suffers from the difficulty of the product forming solid material which then is very difficult to brominate further. Also, the occlusion of sulfuric acid in the solid product results in impurities which are difficult to remove.

The use of Friedel-Crafts catalysts in the classical approach to brominating aromatic compounds results in the production of dibromo derivatives of the aromatic compounds. Certain improvements have been made; for example, see U.S. Pat. No. 3,285,965 in which the aromatics are brominated in a $C_{2-4}$ alkylene dibromide solvent and in the presence of chlorine and a halogenation catalyst. However, up to 20 percent by weight of excess bromine must be used in this process; and the excess bromine is taken up by addition of a $C_{2-4}$ alkylene to produce additional dihalide. The process is difficult to control and requires the use of chlorine to oxidize the HBr back to elemental bromine with the subsequent problem of disposing of HCl. Also, the alkylene must be continuously added to make up solvent losses and quench the excess bromine.

In another process, French Patent 69/002,243, the bromination of biphenyl using $AlCl_3$ catalyst without a solvent is carried out. However, this process suffers from the serious disadvantage of the partially brominated product becoming so viscous that special mixers are required to continue the bromination of the solid material.

In application Ser. No. 120,345 filed Mar. 2, 1971, by Lawrence C. Mitchell now U.S. Pat. No. 3,763,248, an improved method for polybrominated aromatics is described. This application provides a further improvement. More specifically, products produced by the process of this application have less color or lessened tendency to color upon standing than those produced by the process of application Ser. No. 120,345 supra (U.S. Pat. No. 3,763,248). Thus, although the Mitchell process is highly efficacious for bromination of aromatics, the process of the instant invention may be of choice where product specifications require more stringent removal of color forming bodies. A main improvement provided by this invention is the isolation procedure; i.e. isolation of the product via precipitation from the reaction mixture by adding a precipitant, e.g. methanol and the like. Another main improvement are the products produced by the process of this invention.

SUMMARY OF THE INVENTION

This invention pertains to a process for the production of polybrominated aromatic compounds and mixtures thereof having up to about 10 bromine atoms per molecule, said process comprising (a) reacting an aromatic compound with bromine in the presence of a halogenation catalyst and solvent quantities of methylene bromide, and (b) treating the reaction mixture thereby produced with an alkanol of one to 4 carbon atoms to precipitate a polybrominated product.

A highly preferred aromatic starting material is biphenyl. A highly preferred lower alkanol is methanol. Of the catalysts, aluminum chloride, aluminum bromide, mixtures thereof, and ferrous and ferric chlorides, bromides and iodides are preferred. Preferably from 0.001 to 0.01 moles of catalyst are used per mole of bromine.

A highly preferred embodiment is a process for preparing polybrominated biphenyl oxide having 8 to 10 bromine atoms per molecule, said process comprising brominating biphenyl oxide in the presence of a catalytic quantity of a catalyst selected from the class consisting of aluminum halide and iron halide, and in the presence of solvent quantities of methylene bromide, and subsequently adding methanol to the thereby-produced reaction mixture to precipitate said polybrominated biphenyl oxide. Other embodiments are the products produced by this invention's process.

DESCRIPTION OF PREFERRED EMBODIMENTS

The exact nature of the aromatic compounds which may be brominated by the process of this invention is not critical since the invention is applicable to a large variety of aromatic compounds. For example, the prior art shows many types of aromatic compounds which are suitable for bromination. The improved process of this invention utilizes the mono- or polynuclear aromatic compounds having either condensed or separated aromatic nuclei, their partially halogenated derivatives, their normal alkyl-substituted derivatives wherein the alkyl radical has up to 10 carbon atoms, and their branched alkyl-substituted derivatives wherein the branched alkyl radical is not α-substituted and has up to about 10 carbon atoms. Because of their relatively greater availability, aromatics up to about 24 carbon atoms are preferred. Typical of the unsubstituted condensed or separated mono- or polynuclear aromatic compounds are (1) benzene, (2) naphthalene, (3) anthracene, (4) phenanthrene, diphenyl, (5) triphenyl, (6) tetraphenyl, (7) diphenyl benzene, (8) perylene, (9) diphenyl ether, and the like. Typical partially halogenated derivatives may be fluoro-, chloro-, bromo-, or iodo- derivatives; for example, mono-, di-, tri-, and tetra- halogenated derivatives are typical of the partially halogenated compounds. Typical normal alkyl-substituted derivatives are the methyl, ethyl, propyl, butyl pentyl, hexyl, heptyl, octyl, nonyl, and decyl radicals. There may be more than one of such radicals substituted on the aromatic nucleus. The branched alkyl-substituted derivatives may be substituted-pentyl, hexyl, heptyl, octyl, nonyl, and decyl radicals or the 2,2-dimethylpropyl, 2,3-dimethylpropyl, 2-methylbutyl, 2,3-dimethylbutyl, 3,3-dimethylbutyl, 2,2,3,3-tetramethylpentyl, 2-ethylbutyl, 2,3-diethylbutyl, 2-propylbutyl, and like radicals. Preferred aromatic compounds which may be brominated by the improved process are diphenyl, benzene, monochlorobenzene, and toluene. The most preferred aromatic compound for this embodiment is diphenyl oxide.

The above aromatic compounds may be halogenated by the process of this invention using either chlorine or bromine. However, the process of this invention is more advantageously directed to the production of polybrominated aromatic compounds. Thus, it is preferred that bromine is used as the halogenating agent. While any method of introducing the bromine into the reaction system is sufficient provided that no other interfering cations or anions are introduced concurrently, it is preferred that elemental bromine in either liquid or gaseous form is introduced into the reaction medium.

The amount of bromine required for the improved process of this invention depends on the degree of bromination desired in the final product, the amount of catalyst used, and the particular reaction conditions employed. Because this improved process enables one to brominate an aromatic compound to almost any degree desired, the amount of bromine used will vary and is not considered critical, except when one is attempting to produce a brominated aromatic compound having a specific bromine content. It is generally sufficient if a slight excess above the theoretical requirements of the desired polybrominated aromatic compound is used. Thus, the amount of bromine used can range from 4 to about 12 moles of bromine per mole of aromatic compound to be brominated. Of course, the higher end of this ratio is clearly applicable to the more complex aromatic compounds which may be used in this improved process. It is not intended to suggest that 12 moles of bromine can be added to the simpler aromatic compounds; for example, benzene, toluene, xylene, and the like. More preferred amounts of bromine utilized by this improved process are from 6 to about 12 moles of bromine per mole of the aromatic compound to be brominated; such as diphenyl, triphenyl, naphthalene, and their substituted derivatives as hereinabove described. A most preferred amount of bromine is from 7 to 12 moles of bromine per mole of such aromatic compound.

The reaction of bromine with the aromatic compound usually takes place in the liquid phase and is initially exothermic; that is, heat is given off as the reaction occurs. However, after the first few bromine atoms are added, it is advantageous to continue the reaction by adding heat to the reactants. A temperature sufficient to allow a rapid rate of reaction is all that is required. For example, when using liquid bromine, any temperature at which all of the reactants are present in the liquid phase forming a homogeneous mixture, even if such homogeneous reaction mixture must be achieved by increasing the pressure of the reaction system is all that is required. Careful attention should be paid to the conduct of the reaction since the evolution of gas on reaction may be quite violent if the reaction proceeds too fast. It has generally been found that the reaction may be carried out easily at temperatures from room temperature to about 200°C. A preferred temperature range is from room temperature to 100°C.

In the improved process of this invention, the aromatic compound and bromine are reacted in the presence of a halogenation catalyst and methylene bromide. Without the use of a halogenation catalyst, bromination is entirely too slow to be of any practical value. In addition, without the catalyst only one or two bromine atoms per aromatic nucleus can be added. Therefore, a halogenation catalyst is required. It has been found that a metal halide where the metal is selected from aluminum and iron is an especially useful and preferred halogenation catalyst in the improved process of the invention. Particularly preferred are aluminum chloride, aluminum bromide, iron chloride, iron bromide, and mixtures of these. The most preferred catalysts are aluminum chloride, aluminum bromide and mixtures thereof.

The amount of catalyst added depends on the desired degree of bromination. The addition of larger amounts of catalyst allows a higher degree of bromination; but the amount of bromine present is a limiting factor to the degree of bromination. Generally, the catalyst is supplied to the reaction mixture in amounts of from 0.0001 to 0.1 mole of halogenation-catalyst per mole of bromine. However, a preferred amount of catalyst is from 0.001 to 0.01 mole of halogenation catalyst per mole of bromine. A most preferred amount of catalyst for efficient production of the desired polybrominated aromatic compounds is from 0.001 to 0.007 mole per mole of bromine.

In conducting the process of this invention, it has also been found that the use of solvent quantities of methylene bromide allows the reaction to proceed to the point of producing highly brominated aromatic compounds without the product becoming a solid or agglomerating and preventing further bromination. Thus, it can be seen that the improvement of the use of halogenation catalyst and methylene bromide are both necessary to the production of the desired polybrominated aromatic compounds. Generally, sufficient solvent is required to adequately maintain the reactants and brominated products in homogeneous reaction mixtures. However, the reaction mixture should not be so diluted by the solvent as to require uneconomically large reaction vessels and large solvent inventories. Moreover, the temperature at which the reaction is carried out will affect the ability of the solvent to maintain a homogeneous reaction mixture. In view of these considerations the amount of solvent used should range from about saturated with the reactants and brominated products to about 100 moles of solvent per mole of reactants and brominated products. A more convenient method of stating the amount of solvent required is to base the amount solely on the starting aromatic compound to be brominated. Thus, methylene bromide is conveniently supplied in an amount of from about 8 to about 20 moles of methylene bromide per mole of aromatic compound. A more preferred solvent to aromatic compound ratio is from 10 to about 15 moles per mole of aromatic compound.

The time required for the reaction to go to completion depends upon the rate of reaction and the degree of bromination desired. It has been found that the reaction can be completed in as little as two hours and can continue for as long as 24 hours. Another limiting factor is the ability of the reaction vessel to handle the amount of gas evolved and thus allow rapid addition of the halogenation catalyst. In a highly efficient reaction system it is possible therefore for the reaction to be carried out to the desired degree of bromination in less than 2 hours. While the reaction time is not critical, it is preferred to carry out the reaction from about 2 to about 10 hours.

The product consists of the polybrominated aromatic compound in the solvent with unreacted bromine and small amounts of catalyst and partially brominated aromatic compound. When the desired degree of bromination has been obtained, the reaction may be stopped by cooling.

In the process of this invention, the product is isolated from the reaction mixture by precipitation with a precipitating agent. The precipitation can be conducted with an acid washed reaction mixture but it is not necessary to do so. The precipitating agent can be added directly to the reaction mixture.

The precipitating agent can be any substance which causes the desired product to become separated from the liquid phase resultant by adding the agent to the reaction mixture. Highly preferred precipitating agents are those which cause separation of the product with a reduced quantity of colored impurities, or impurities which cause color formation on standing.

The precipitating agent can be a lower alkanol of one to four carbons such as ethanol, n-propanol, isopropanol, n-butanol, and its isomers. Methanol is preferred.

In general, an amount of precipitating agent is used which causes the desired phase separation to take place. There is no real upper limit on the amount, this being governed by such secondary considerations as economics, and vessel size. In general, for each volume of reaction mixture, from about 1 to about 4 volumes of precipitating agent are used; greater and lesser amounts can be used if desired.

The temperature at which the reaction mixture and precipitating agent are admixed is not critical. Any convenient temperature can be used. Thus, sub-ambient, ambient and elevated temperatures can be employed; room temperature and elevated temperatures being preferred. A preferred range is from ambient temperature to the reflux temperature. For example, when methanol is used, room temperature to 65°C. can be used.

In some instances it may be advantageous to concentrate the reaction mixture say by removing methylene bromide solvent. For example, one may wish to add methanol to a reaction mixture which has been concentrated to the stage at which brominated product is about to precipitate.

After precipitation, the product can be maintained in contact with the resultant liquid phase for say up to one hour, to assist precipitation of final amounts in solution. Alternatively, the filtrate can be quickly removed, if desired. After precipitation, the product can be washed with additional alkanol or caustic solution, if desired. The caustic concentration is not critical and 5–15 weight percent will suffice. Washing with these substances tends to remove colored or color forming materials remaining in minor amounts in the separated product.

If product specifications regarding absence of color are particularly stringent, or in cases where it is somewhat difficult to remove product color, it may be advantageous to perform one or more of the following:
1. Employ $CH_2Br_2$ and precipitants that have been distilled and kept from exposure to light.
2. Conduct the bromination in the absence of light.
3. Precipitate product from the reaction mixture in the dark.
4. Keep the reaction temperature at a minimum level which affords a reasonable rate, or otherwise prevent or minimize having reactants or products at temperatures at which color formation is appreciable. Thus, for example, in preparing polybrominated diphenyls, better results are obtained if the time the reaction mixture is kept above 90°C. is kept to a minimum, preferably 30 minutes or less.

EXAMPLE 1

Biphenyl oxide (88.2 g, 0.518 M) is dissolved in methylene bromide (750 g.) and bromine (870 g, 5.43 M, 5% excess) is added over 30 minutes at 15°–18°C (external cooling). A solution of aluminum bromide (7.5 g) in methylene bromide (250 g) is added to the reaction mixture over about 3 hours at 20°–90°C. After a total of 50 minutes at 90°, the mixture is cooled to ca. 80°C, when methanol (1200 ml) is added keeping the mixture at 60°–65°C. The mass is cooled to ambient temperature, filtered, and washed twice with methanol to give decabromobiphenyl oxide.

The product can contain other materials such as octabromobiphenyl oxide, and nonabromobiphenyl oxide.

Similar results are obtained when the alkanol is ethanol, isopropanol or sec-butanol.

Similar results are obtained using aluminum chloride, a mixture of equal weights $AlCl_3$ and $AlBr_3$, $FeCl_2$, $FeCl_3$, $FeBr_2$, $FeBr_3$ and iron metal and iodine powder as a catalyst, 0.001 to 0.01 moles of catalyst per mole of bromine.

Similar results are obtained using a reaction temperature of ambient to 100°C.

EXAMPLE 2

To a reaction vessel, fitted with an ampule for adding a solid catalyst, was added 17.8 parts of biphenyl and 197.5 parts of methylene bromide. The ampule was filled with 2.3 parts of $AlBr_3$. The $AlBr_3$ was slowly added to the reaction vessel over a period of 2 hours and 25 minutes with slow heating from room temperature to about 75°C. After the catalyst was added, heating was continued for about 2 hours and 25 minutes up to 96°C. The evolution of HBr gas was evidence of reaction during the entire period.

The heating was discontinued and sufficient 10 percent HCl solution was added to stop the reaction. The solution turned rust colored and was separated into an organic phase and an aqueous phase. The organic layer was washed twice with water and examined by vapor phase chromatograph. The only known peaks were solvent and biphenyl. No crystalline polybrominated product could be isolated. Work-up of the reaction product and examination by infrared spectroscopy and NMR indicated that oligomers containing biphenyl moieties connected by methylene bridges were present. Such products would be expected in Friedel-Crafts alkylation.

The above example illustrates that the methylene bromide will react with diphenyl to give unspecified products. However, in the presence of bromine the reaction to produce polybrominated aromatics is much faster and $CH_2Br_2$ does not react at a rate sufficient to alkylate the aromatic nucleus. In view of the reaction in Example 2 above, the bromination being exclusive is indeed extremely surprising.

Many compounds produced by the process of this invention are well known for their use as flame-retardant additives, see U.S. Pat. No. 3,285,965, as liquid dielectrics, see U.S. Pat. No. 2,977,516, as flame resistant electric conductor insulation additives, see U.S. Pat. No. 1,863,147, as heat transfer media, lubricants and like applications wherein high thermal stability and/or flame resistance are advantageous.

The process of this invention as described in the foregoing specification is illustrative and not intended to limit the scope of the following claims.

I claim:

1. A process for preparing polybrominated biphenyl oxide having 8 to 10 bromine atoms per molecule, said process comprising reacting biphenyl oxide with bromine at a temperature of from room temperature to about 200°C in the presence of 0.001 to 0.1 moles of catalyst per mole of bromine, said catalyst selected from the class consisting of aluminum chloride, aluminum bromide, iron chloride, and iron bromide, and mixtures thereof, and in the presence of methylene bromide, as the reaction solvent, and subsequently treating the reaction mixture at reflux with methanol to precipitate polybrominated biphenyl oxide.

2. A process of claim 1 wherein said halogenation catalyst is selected from $AlCl_3$, $AlBr_3$, and mixtures thereof.

3. A process of claim 2 wherein said halogenation catalyst is $AlBr_3$.

4. A process of claim 2 wherein said halogenation catalyst is $AlCl_3$.

* * * * *